United States Patent [19]

White et al.

[11] 4,113,768

[45] Sep. 12, 1978

[54] PREPARATION OF ACRYLIC OR METHACRYLIC ACID FROM ACROLEIN OR METHACROLEIN

[75] Inventors: James F. White, Akron; Michael D. Applequist, Mayfield Heights, both of Ohio

[73] Assignee: The Standard Oil Company, Cleveland, Ohio

[21] Appl. No.: 748,081

[22] Filed: Dec. 6, 1976

Related U.S. Application Data

[63] Continuation-in-part of Ser. No. 701,259, Jun. 30, 1976, abandoned.

[51] Int. Cl.² ............................................. C07C 51/32
[52] U.S. Cl. ................................... 562/535; 252/435; 252/437; 562/534
[58] Field of Search ................... 260/530 N; 252/435, 252/437

[56] References Cited

U.S. PATENT DOCUMENTS

3,976,688  8/1976  Akiyama et al. ................ 260/530 N

*Primary Examiner*—Vivian Garner
*Attorney, Agent, or Firm*—Gwenetta Douglas Hill; Herbert D. Knudsen; Larry William Evans

[57] ABSTRACT

Methacrylic acid or acrylic acid are produced by the oxidation of methacrolein or acrolein, respectively, with molecular oxygen in the vapor phase in the presence of a catalytic oxide of molybdenum, phosphorus, bismuth, copper, oxygen, optionally a halogen selected from the group consisting of chlorine, bromine or iodine, and optionally, at least one element selected from the group consisting of Fe, Cr, Ni, Mn, Sb, Te, Rh, and Pd.

20 Claims, No Drawings

PREPARATION OF ACRYLIC OR METHACRYLIC ACID FROM ACROLEIN OR METHACROLEIN

REFERENCE TO RELATED APPLICATIONS

This is a continuation-in-part of our earlier application, U.S. Ser. No. 701,259, filed June 30, 1976, now abandoned.

BACKGROUND OF THE INVENTION

A number of catalysts are known to be effective for the oxidation of acrolein or methacrolein to acrylic acid or methacrylic acid, respectively. However, the yields obtained using the catalysts for the preparation of methacrylic acid are low. The present invention is a result of a search for more efficient and desirable catalysts for the production of acrylic acid and methacrylic acid. Unexpected higher yields of and selectivities to acrylic acid and methacrylic acid are obtained by the vapor phase oxidation of acrolein and methacrolein, respectively, with molecular oxygen in the presence of the new and useful catalysts of the present invention.

SUMMARY OF THE INVENTION

It has been discovered according to the present invention in the process for the preparation of acrylic acid or methacrylic acid by the oxidation of acrolein or methacrolein, respectively, with molecular oxygen in the vapor phase at a reaction temperature of about 200° C to about 500° C in the presence of an oxide catalyst, and optionally in the presence of steam, the improvement comprising using as a catalyst a catalyst of the formula $$Mo_{12}P_aBi_bCu_cM_dX_eO_f$$

wherein M is at least one element selected from the group consisting of iron, chromium, nickel, manganese, tellurium, palladium, antimony, and rhodium;

X is a halogen selected from the group consisting of chlorine, bromine, or iodine;

and wherein $a$, $b$, and $c$ are numbers from 0.001 to 10;
$d$ is from 0 to 10;
$e$ is 0 to 5;
$f$ is a positive number of oxygens required to satisfy the valence states of the other elements present.

The surprisingly advantageous catalysts of this invention give improved yields of acrylic acid and methacrylic acid from acrolein and methacrolein, respectively, in an efficient, convenient, and economical manner at a relatively low temperature. The exotherm of the reaction is low, thereby allowing easy reaction control.

The most significant aspect of the present invention is the catalyst employed. The catalyst may be any of the catalysts delineated by the above formula. The catalysts can be prepared by a number of different techniques described in the art, such as coprecipitation of soluble salts and calcination of the resulting product.

The catalysts of the invention have preferred limitations on their composition. Preferred are catalysts wherein $a$, $b$, and $c$ are numbers from 0.01 to 5 and $e$ is from 0 to 1.0. Also preferred are catalysts wherein $a$ is 1 to 1.5, catalysts wherein $b$ is 0.1 to 0.5, catalysts wherein $c$ is 0.1 to 1.0, and catalysts wherein $e$ is 0.01 to 0.5. Especially preferred are catalysts wherein $e$ is 0.01 to 0.20, and catalysts wherein $d$ is zero. Especially preferred are catalysts wherein X is chlorine. Catalysts of special interest are described wherein chlorine, bromine, or iodine is present as an essential catalytic component. Especially preferred are catalysts wherein chlorine is a required component.

In the catalyst preparations, the various elements of the catalyst are combined, and the final product is calcined to obtain the catalyst. A number of methods of combining the elements of the catalyst and calcining the resultant product are known to those of skill in the art. In the broad concept of the invention, the particular method of preparing the catalysts is not critical.

There are, however, methods of preparing the catalysts that have been found to be preferred. One preferred preparation involves the preparation of the catalysts in an aqueous slurry or solution of molybdenum and/or phosphorus containing components, and adding the remaining components; evaporation of this aqueous mixture; and calcination of the resulting catalysts. Suitable molybdenum compounds that may be employed in the preparation of the catalysts delineated by the above formula include molybdenum trioxide, phosphomolybdic acid, molybdic acid, ammonium heptamolybdate and the like. Suitable phosphorus compounds that may be employed in the preparation of the catalysts include ortho phosphoric acid, metaphosphoric acid, triphosphoric acid, phosphorous pentabromide, phosphorus pentachloride, and the like. The remaining components of the catalysts may be added as oxide, acetate, formate, sulfate, nitrate, carbonate, oxyhalide, or halide and the like.

The catalysts of this invention also may be prepared by mixing the catalytic components in an aqueous slurry or solution, heating the aqueous mixture to dryness and calcining the resulting catalysts.

Excellent results are obtained by refluxing phosphoric acid and molybdenum trioxide in water for about 1.5 to 3 hours, however, commercial phosphomolybdic acid may be effectively utilized; adding the remaining components to the aqueous slurry and boiling to a thick paste, where at least one of the components is added as a halide or oxyhalide; drying at 110° to 120° C in air; and calcining the resulting catalysts. It is not clearly understood where the halogen atom is located in the catalytic structure. Infra-red and X-ray analysis reveals that the catalysts are mostly phosphomolybdate-based and that the halogen may be present as a molybdenum oxyhalide.

Excellent results are obtained using a coated catalyst consisting essentially of an inert support material having a diameter of at least 20 microns and an outer surface, and a continuous coating of said active catalyst on said inert support strongly adhering to the outer surface of said support. The special coated catalyst consists of an inner support material having an outer surface and a coating of the active catalytic material on this outer surface.

The support material for the catalyst forms the inner core of the catalyst. This is an essentially inert support and may have substantially any particle size although a diameter of at least 20 microns is preferred. Especially preferred in the present invention for use in a commercial reactor are those supports which are spherical and which have a diameter of about 0.2 cm. to about 2 cm. Suitable examples of essentially inert support materials include: Alundum, silica, alumina, alumina-silica, silicon carbide, titania and zirconia. Especially preferred among these supports are Alundum, silica, alumina and alumina-silica.

The catalysts may contain essentially any proportion of support and catalytically active material. The limits of this relationship are only set by the relative ability of the catalyst and support material to accommodate each other. Preferred catalysts contain about 10 to about 100 percent by weight of catalytically active material based on the weight of the support.

The preparation of these coated catalysts can be accomplished by various techniques. The basic method of preparing these catalysts is to partially wet the support material with a liquid. The support cannot be wet on the outside surface of the total mass. It should be dry to the touch. If the support is wet, then the active catalytic material will agglomerate into separate aggregates when coating of the support is attempted. These partially wet supports are then contacted with a powder of the catalytically active material and the mixture is gently agitated until the catalyst is formed. The gentle agitation is most conveniently conducted by placing the partially wet support in a rotating drum and adding the active catalytic material until none is taken up by the support. This is very economically done.

The calcination of the catalyst usually is accomplished by heating the dry catalytic components at a temperature of about 300° to about 700° C. For example, the catalyst can be calcined at 325°–450° C in air. The particular calcination for the most desirable results varies as the different catalysts are prepared. The best calcination conditions for catalysts of the invention are shown in the Specific Embodiments.

The reactants of the reaction of the invention are methacrolein and oxygen. Molecular oxygen is normally supplied to the reaction in the form of air, but oxygen gas could also be employed. About 0.5 to about 4 moles of oxygen are normally added per mole of methacrolein.

The reaction temperature may vary as different catalysts are employed. Normally, temperatures of about 200° to about 500° C are employed with temperatures of 250° to 370° C being preferred.

The reaction is conveniently conducted in either a fixed-bed or fluid-bed reactor. The contact time may be as low as a fraction of a second or as high as 20 seconds or more. The reaction may be conducted at atmospheric, superatmospheric or subatmospheric pressure, with absolute pressures of about 0.5 to about 4 atmosphere being preferred.

When used in the reactor, the catalyst may be in a supported or unsupported form. Suitable support materials include, Alundum, silica, alumina, boron phosphate, zirconia, silicon carbide, or titania.

When the catalysts are reacted with acrolein or methacrolein in a fixed-bed reactor, the active catalytic components may be coated on an inert support; however, in the alternative, the active catalytic ingredients may be mixed with one of the above support materials prior to coating the inert support.

It is also contemplated by the present invention that acrolein or methacrolein may be oxidized by the instant vapor phase catalytic reaction using the catalysts of the invention provided that a minor quantity of chlorine, iodine, or bromine or an inorganic or organic halide is incorporated in the feed.

Using the catalysts of the invention in the preparation of methacrylic acid or acrylic acid, excellent yields are obtained in a convenient reaction with low amounts of byproducts.

SPECIFIC EMBODIMENTS

Examples 1 to 9

Various catalysts of the invention were prepared as follows:

EXAMPLE 1

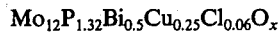
$Mo_{12}P_{1.32}Bi_{0.5}Cu_{0.25}Cl_{0.06}O_x$

Part A.

A slurry was prepared of 86.4 (0.06 mole Mo) of molybdenum trioxide and 7.6 g. (0.067 mole P) of 85% phosphoric acid in 500 mls. of distilled water; boiled with stirring for three hours to form phosphomolybdic acid which was yellowish green in color. To this slurry was added 2.5 g. (0.0125 mole Cu) of copper acetate; no change in color, followed by the addition of 7.9 g. (0.025 mole Bi) of bismuth chloride dissolved in 4.0 ml. of concentrated hydrochloric acid. The mixture was boiled to dryness; dried overnight at 110° C in air. The catalyst was ground and screened to 20/30 mesh fraction and calcined for three hours at 400° C in 40 ml/min. air.

Part B.

A large-size batch of this catalyst was prepared using 3500 mls. distilled water, 432 grams of molybdenum trioxide, 38 grams of phosphoric acid, 12.5 grams of copper acetate, 39.5 grams of bismuth chloride dissolved in 25 mls. of concentrated hydrochloric acid. The mixture was heated overnight at 75° C; boiled to dryness; dried overnight at 110° C in an oven; ground and screened; and calcined for three hours at 400° C in 40 ml/min air.

EXAMPLES 2 TO 9

These catalysts were calcined in the same manner described in Example 1.

EXAMPLE 2

$Mo_{12}P_{1.32}Bi_{0.5}Cu_{0.25}Cl_{0.04}O_x$

This catalyst was prepared in the same manner as in Example 1, Part B.

EXAMPLE 3

$Mo_{12}P_{1.32}Bi_{0.5}Cu_{0.25}Cl_{0.05}O_x$

This catalyst was prepared in the same manner as in Example 1, except the molybdenum trioxide and phosphoric acid were replaced with 118.3 g. of commercially available phosphomolybdic acid and 1.84 g. of 85% phosphoric acid.

EXAMPLE 4

$Mo_{12}P_{1.32}Bi_{0.5}Cu_{0.25}Cl_{0.055}O_x$

This catalyst was prepared in the same manner as in Example 1, except that the hydrochloric acid was replaced with 15 mls. of concentrated nitric acid.

EXAMPLE 5

$Mo_{12}P_{1.32}Bi_{0.5}Cu_{0.25}Cl_{0.06}O_x$

This catalyst was prepared in the same manner as in Example 1, except the bismuth chloride was replaced with 5.8 g. (.025 mole Bi) of bismuth oxide.

EXAMPLE 6

$Mo_{12}P_{1.32}Bi_{0.5}Cu_{0.25}O_x$

This catalyst was prepared in the same manner as in Example 1, except no halogen was employed in the preparation. The bismuth chloride was replaced with 5.8 g. (.025 mole Bi) of bismuth oxide and hydrochloric acid was not employed in the preparation.

EXAMPLE 7

$Mo_{12}P_{1.32}Bi_{0.5}Cu_{0.25}O_x$

This catalyst was prepared in the same manner as in Example 6, except the bismuth oxide was replaced with 12.1 g. of $Bi(NO_3)_3 \cdot 5H_2O$.

EXAMPLE 8

$Mo_{12}P_{1.32}Cu_{0.15}Bi_{0.3}Fe_{0.1}Cr_{0.1}Ni_{0.1}Cl_{0.04}O_x$

A slurry was prepared from 86.4 g. (0.60 mole Mo) molybdenum trioxide and 7.6 g. (0.067 mole P) of 85% phosphoric acid in 500 mls. of distilled water. To this slurry was added 1.5 g. (0.0075 moles Cu) of copper acetate, 4.8 g. (0.015 mole Bi) of bismuth chloride, 5.0 mls. of concentrated hydrochloric acid, 1.4 g. (0.005 mole Fe) of ferric chloride hydrate, 0.4 g. (0.005 mole Cr) of chromium oxide and 0.9 g. (0.005 mole Ni) of nickel acetate.

EXAMPLE 9

$Mo_{12}P_{1.32}Cu_{0.2}Bi_{0.4}Sb_{0.1}Ni_{0.05}Cl_{0.04}O_x$

A slurry was prepared from 86.4 g. (0.60 mole Mo) of molybdenum trioxide and 7.6 g. (0.067 mole P) of 85% phosphoric acid in 500 mls. of distilled water and refluxed for 3 hours with heating; the color was yellowish green.

To this slurry was added 0.7 g. (0.005 mole Sb) of antimony oxide; the color changed to dark green, and then was added 2.0 g. (0.01 mole Cu) of copper acetate, 6.3 g. (0.02 mole Bi) of bismuth chloride, 3.5 mls. of concentrated hydrochloric acid and 0.4 g. (0.0025 mole Ni) of nickel acetate.

EXAMPLES 10 to 18

Preparation of methacrylic acid using various catalysts of the invention.

The catalysts were prepared in the same manner as shown above using the appropriate ratios of ingredients.

A portion of these catalyst particles were charged to a 20 cc. fixed-bed reactor consisting of a 1.3 cm. stainless steel tubing equipped with a 0.3 cm. axial thermowell. The reactor was heated to reaction temperature under a flow of air and a feed of methacrolein/air/steam of 1/6.2/5.2 and was fed over the catalyst at an apparent contact time of 4 to 5 seconds. The reactor was run under the reaction conditions for 1 to 5 hours and the product was collected and analyzed. The reaction conditions and results of the experiments are shown in TABLE I. The following definitions are used in measuring the carbon atoms in the feed and the products.

$$\% \text{ single pass yield} = \frac{\text{Moles of Methacrylic Acid Recovered}}{\text{Moles of Methacrolein in the feed}} \times 100$$

$$\text{Total Conversion} = \frac{\text{Moles of Methacrolein Reacted}}{\text{Moles of Methacrolein in the feed}} \times 100$$

$$\text{Selectivity} = \frac{\text{Single Pass Yield}}{\text{Total Conversion}} \times 100$$

TABLE I
PREPARATION OF METHACRYLIC ACID USING VARIOUS CATALYSTS OF THE INVENTION

| | | | Results, % | | | | |
|---|---|---|---|---|---|---|---|
| Ex. | Catalyst | Reaction Temp.° C | Single Pass Yield Methacrylic Acid | Single Pass Yield Acetic Acid | Selectivity Methacrylic Acid | Total Conversion | Catalyst Preparation Employed: |
| 10 | $Mo_{12}P_{1.32}Bi_{0.5}Cu_{0.25}Cl_{0.06}O_f$ | 316 | 69.4 | 3.5 | 79.5 | 87.3 | $BiCl_3$ + HCl |
| 11 | $Mo_{12}P_{1.32}Bi_{0.5}Cu_{0.25}Cl_{0.06}O_f$ | 313 | 70.4 | 6.6 | 74.6 | 94.5 | $BiCl_3$ + HCl (large batch size) |
| 12 | $Mo_{12}P_{1.32}Bi_{0.5}Cu_{0.25}Cl_{0.05}O_f$ | 302 | 63.9 | 5.8 | 73.0 | 87.6 | Commercially available PMA + $BiCl_3$ + HCl |
| 13 | $Mo_{12}P_{1.32}Bi_{0.5}Cu_{0.25}Cl_{0.055}O_f$ | 337 | 40.3 | 7.9 | 61.1 | 65.9 | $BiCl_3$ + $HNO_3$ |
| 14 | $Mo_{12}P_{1.32}Bi_{0.5}Cu_{0.25}Cl_{0.06}O_f$ | 316 | 52.0 | 4.1 | 74.4 | 70.0 | $Bi_2O_3$ + HCl |
| 15 | $Mo_{12}P_{1.32}Bi_{0.5}Cu_{0.25}O_f$ | 330 | 38.0 | 8.0 | 59.0 | 65.4 | $Bi_2O_3$; no halogen |
| 16 | $Mo_{12}P_{1.32}Bi_{0.5}Cu_{0.25}O_f$ | 350 | 28.3 | 9.9 | 50.3 | 56.2 | $Bi(NO_3)_3 \cdot 5H_2O$ no halogen |
| 17 | $Mo_{12}P_{1.32}Cu_{0.15}Bi_{0.3}Fe_{0.1}Cr_{0.1}Ni_{0.1}Cl_{0.04}O_x$ | 330 | 61.9 | 3.8 | 76.7 | 80.7 | $BiCl_3$ + HCl |
| 18 | $Mo_{12}P_{1.32}Cu_{0.20}Bi_{0.4}Sb_{0.1}Ni_{0.05}Cl_{0.04}O_f$ | 313 | 64.9 | 4.4 | 79.5 | 81.6 | $BiCl_3$ + HCl |

EXAMPLES 19 TO 21

Effect of reaction temperature and proper calcination of the catalysts in the preparation of methacrylic acid using the catalyst $Mo_{12}P_{1.32}Bi_{0.5}Cu_{0.25}Cl_{0.04}O_x$.

EXAMPLES 19 TO 20

The catalyst of Example 2 was calcined in the absence of air flow for 3 hours at 400° C and subsequently was reacted with methacrolein at 343° C. A second run was made at 377° C.

EXAMPLE 21

The catalyst of Example 2 was reacted in the same manner as in Example 19, except it was calcined in air and subsequently was reacted with methacrolein at 313° C.

These experimental results are found in Table II.

TABLE II
EFFECT OF PROPER CALCINATION AND REACTION TEMPERATURE USING THE CATALYST
$Mo_{12}P_{1.32}Bi_{0.5}Cu_{0.25}Cl_{0.04}O_x$

| | | Results, % | | |
|---|---|---|---|---|
| Example | Calcination | Single Pass Yield | Selectivity | Total Conversion |
| 19 | without air | 7.9 | 60 | 13.1 |
| 20 | without air | 14.1 | 80 | 17.5 |

TABLE II-continued
EFFECT OF PROPER CALCINATION AND REACTION TEMPERATURE USING THE CATALYST $Mo_{12}P_{1.32}Bi_{0.5}Cu_{0.25}Cl_{0.04}O_x$

| | | Results, % | | |
|---|---|---|---|---|
| Example | Calcination | Single Pass Yield | Selectivity | Total Conversion |
| 21 | in air | 66.7 | 73 | 91.5 |

Thus, the reaction temperature coupled with proper calcination of the catalysts are critical in obtaining desirable yields of methacrylic acid by the process of the invention.

EXAMPLES 22 TO 28

Preparation of Methacrylic Acid Using Catalysts of the Invention:

EXAMPLE 22

A catalyst of the formula 20% $Mo_{12}P_{1.32}Bi_{0.5}Cu_{0.25}Cl_{0.07}O_f$ + 80% Alundum was prepared as follows:

A solution consisting of 105.9 grams of ammonium heptamolybdate, $(NH_4)_6Mo_7O_{24}\cdot 4H_2O$, (0.6 mole M), and 500 mls. of distilled water was boiled with stirring. To this solution was added 7.9 grams of bismuth chloride, $BiCl_3$ (0.025 mole Bi) as a solution in 15 mls. of concentrated hydrochloric acid; to this solution was added 2.5 grams of copper acetate (0.0125 mole Cu), 7.7 grams of phosphoric acid (0.066 mole P), and 2.5 grams of hydrazine hydrate. The mixture was boiled to dryness and dried overnight at 110° C. This material was ground and screened to less than 80 mesh size and then coated onto Norton SA 5223 ⅛ inch Alundum balls by taking 50 grams of Alundum, wetting the Alundum with 1.8 grams of water and adding 16.7 grams of the powdered material in five equal portions. During and after each addition, the Alundum was rolled in a glass jar. The resulting product was then dried in an oven at 110°–120° C overnight.

EXAMPLE 23

20%$Mo_{12}P_{1.32}Bi_{0.5}Cu_{0.25}Cl_{0.16}O_f$ + 80% Alundum

This catalyst was prepared in the same manner described above, except that hydrazine hydrate was deleted.

EXAMPLE 24

15%$Mo_{12}P_{1.32}Bi_{0.5}Cu_{0.25}Cl_{0.06}O_f$ + 85% Alundum

The active catalytic material was prepared in the same manner described in Example 1, Part A, ground and screened to less than 50 mesh; and then coated onto Norton 5223 ⅛ inch Alundum balls by taking 25 grams of Alundum, wetting the Alundum with 1.3 grams of water and adding 4.17 grams of the powdered catalytic material in a single portion. This resulting material was then dried in an oven at 125° C overnight.

EXAMPLE 25

25%$Mo_{12}P_{1.32}Bi_{0.5}Cu_{0.75}Cl_{0.06}O_f$ + 75% Alundum

This catalyst was prepared in the same manner described in Example 24, except that the Alundum was wetted with 1.8 grams of water of 6.94 grams of the powdered catalytic material were added in two equal portions.

EXAMPLE 26

40%$Mo_{12}P_{1.32}Bi_{0.5}Cu_{0.25}Cl_{0.06}O_f$ + 60% Alundum

This catalyst was prepared in the same manner described in Example 24, except the Alundum was wetted with 2.1 grams of water and 11.1 grams of the powdered catalytic material were added in three equal portions. The catalyst was then dried in an oven at 110° C overnight.

EXAMPLE 27

25%$Mo_{12}P_{1.32}Bi_{0.5}Cu_{0.25}Cl_{0.06}O_x$ + 75% Alundum

The active catalytic material was prepared in the same manner described in Example 1, Part B; ground and screened to less than 50 mesh; and then coated onto 10/30 mesh particles of Norton SA 5223 Alundum by taking 50 grams of the 10/30 mesh Alundum, wetting the Alundum with 4 grams of water and adding 16.7 grams of the powdered catalytic material in three-3 grams portions and one-6.7 grams portion. This resulting material was dried at 110°–120° C.

EXAMPLE 28

35%$Mo_{12}P_{1.32}Bi_{0.5}Cu_{0.25}Cl_{0.06}O_x$ + 65% Alundum

This catalyst was prepared in the same manner described in Example 27, except the Alundum was wetted with 2.2 grams of water and 26.9 grams of less than 80 mesh powdered catalytic material were added in 4 equal portions.

EXAMPLES 29 TO 48

Preparation of methacrylic acid using various coated catalysts of the invention.

The catalysts were prepared in the same manner shown above using the appropriate ratios of ingredients. The resulting products were calcined for three hours at 400° C in air to form the active catalysts which consisted of the Alundum support with a continuous, strongly adhering coating of the active catalyst.

Each catalyst prepared in Examples 22 to 28 was charged to the reactor described in Examples 10 to 18. The reactor was heated to reaction temperature under a flow of air and then a feed ratio of methacrolein/air/steam/nitrogen of 1/5.3/5.6/4.6 was fed over the catalyst at an apparent contact time of 2.5 to 2.7 seconds. The reaction conditions and results of the experiments are shown in TABLE III.

TABLE III
PERFORMANCE OF COATED CATALYSTS IN THE PREPARATION OF METHACRYLIC ACID

| Example | Catalyst | Reaction Temp° C | Results, % | | | |
|---|---|---|---|---|---|---|
| | | | Methacrylic Acid | Acetic Acid | Total Conversion | Selectivity |
| 29 reduced | 20%$Mo_{12}P_{1.32}Bi_{0.5}Cu_{0.25}Cl_{0.07}O_f$ + 80% Alundum | 302 | 40.6 | 1.5 | 48.0 | 84.0 |
| 30 | 20%$Mo_{12}P_{1.32}Bi_{0.5}Cu_{0.25}Cl_{0.07}O_f$ + 80% Alundum | 327 | 64.0 | 3.6 | 78.0 | 82.0 |
| 31 | 20%$Mo_{12}P_{1.32}Bi_{0.5}Cu_{0.25}Cl_{0.07}O_f$ + 80% Alundum | 337 | 68.3 | 4.6 | 86.7 | 79.0 |

TABLE III-continued
PERFORMANCE OF COATED CATALYSTS IN THE PREPARATION OF METHACRYLIC ACID

| Example | Catalyst | Reaction Temp° C | Methacrylic Acid | Acetic Acid | Total Conversion | Selectivity |
|---|---|---|---|---|---|---|
| 32 | 20%$Mo_{12}P_{1.32}Bi_{0.5}Cu_{0.25}Cl_{0.07}O_f$ + 80% Alundum | 352 | 68.0 | 5.9 | 90.8 | 75.0 |
| 33 unreduced | 20%$Mo_{12}P_{1.32}Bi_{0.5}Cu_{0.25}Cl_{0.16}O_f$ + 80% Alundum | 302 | 38.0 | 1.3 | 43.0 | 87.0 |
| 34 | 20%$Mo_{12}P_{1.32}Bi_{0.5}Cu_{0.25}Cl_{0.16}O_f$ + 80% Alundum | 327 | 60.0 | 2.7 | 70.0 | 85.0 |
| 35 | 20%$Mo_{12}P_{1.32}Bi_{0.5}Cu_{0.25}Cl_{0.16}O_f$ + 80% Alundum | 338 | 66.0 | 3.5 | 79.9 | 83.0 |
| 36 | 20%$Mo_{12}P_{1.32}Bi_{0.5}Cu_{0.25}Cl_{0.16}O_f$ + 80% Alundum | 352 | 69.4 | 4.5 | 87.0 | 80.0 |
| 37 Ex. 1, Part A | 25%$Mo_{12}P_{1.32}Bi_{0.5}Cu_{0.25}Cl_{0.06}O_f$ + 75% Alundum | 327 | 30.8 | 1.5 | 37.0 | 83.0 |
| 38 | 25%$Mo_{12}P_{1.32}Bi_{0.5}Cu_{0.25}Cl_{0.06}O_f$ + 75% Alundum | 351 | 48.3 | 2.8 | 60.0 | 80.0 |
| 39 | 25%$Mo_{12}P_{1.32}Bi_{0.5}Cu_{0.25}Cl_{0.06}O_f$ + 75% Alundum | 377 | 55.7 | 5.4 | 77.4 | 72.0 |
| 40 Ex. 1, Part A | 15%$Mo_{12}P_{1.32}Bi_{0.5}Cu_{0.25}Cl_{0.06}O_f$ + 85% Alundum | 315 | 49.5 | 3.9 | 64.0 | 78.0 |
| 41 | 15%$Mo_{12}P_{1.32}Bi_{0.5}Cu_{0.25}Cl_{0.06}O_f$ + 85% Alundum | 351 | 36.5 | 1.9 | 43.0 | 84.0 |
| 42 | 40%$Mo_{12}P_{1.32}Bi_{0.5}Cu_{0.25}Cl_{0.06}O_f$ + 60% Alundum | 325 | 49.2 | 2.6 | 60.4 | 81.0 |
| 43 | 40%$Mo_{12}P_{1.32}Bi_{0.5}Cu_{0.25}Cl_{0.06}O_f$ + 60% Alundum | 349 | 63.2 | 5.8 | 85.3 | 74.0 |
| 44 Ex. 1, Part B | 25%$Mo_{12}P_{1.32}Bi_{0.5}Cu_{0.25}Cl_{0.06}O_f$ + 75% Alundum | 315 | 60.9 | 1.7 | 68.6 | 89.0 |
| 45 | 25%$Mo_{12}P_{1.32}Bi_{0.5}Cu_{0.25}Cl_{0.06}O_f$ + 75% Alundum | 343 | 64.0 | 5.6 | 90.0 | 71.0 |
| 46 | 25%$Mo_{12}P_{1.32}Bi_{0.5}Cu_{0.25}Cl_{0.06}O_f$ + 75% Alundum | 365 | 63.2 | 4.6 | 89.0 | 71.0 |
| 47 Ex. 1, Pat B | 35%$Mo_{12}P_{1.32}Bi_{0.5}Cu_{0.25}Cl_{0.06}O_f$ + 65% Alumdum | 341 | 63.0 | 4.8 | 78.0 | 80.0 |
| 48 | 35%$Mo_{12}P_{1.32}Bi_{0.5}Cu_{0.25}Cl_{0.06}O_f$ + 65% Alundum | 348 | 60.8 | 8.1 | 85.0 | 71.5 |

EXAMPLE 49

In the same manner described in Examples 10 to 18, acrylic acid was prepared from acrolein using the catalyst of Example 1, Part A, $Mo_{12}P_{1.32}Bi_{0.5}Cu_{0.25}Cl_{0.06}O_f$. The results of this experiment revealed a 75.1% per pass conversion to acrylic acid, 85.3% total conversion, and 88.0% selectivity at a reaction temperature of 317° C.

We claim:

1. In a process for the preparation of acrylic acid or methacrylic acid by the oxidation of acrolein or methacrolein, respectively, with molecular oxygen in the vapor phase at a reaction temperature of about 200° C to about 500° C in the presence of an oxide catalyst, and optionally in the presence of steam, the improvement comprising using as the catalyst a catalyst of the formula $$Mo_{12}P_aBi_bCu_cM_dX_eO_f$$

wherein M is at least one element selected from the group consisting of iron, chromium, nickel, manganese, tellurium, palladium, antimony, rhodium, or mixtures thereof;

X is a halogen selected from the group consisting of chlorine, bromine, or iodine;

and wherein $a$, $b$, and $c$ are numbers from 0.001 to 10;

$d$ is from 0 to 10;

$e$ is from 0 to 5;

$f$ is a positive number of oxygens required to satisfy the valence states of the other elements present.

2. The process of claim 1 wherein the catalyst is calcined at a temperature of 325°–450° C in air.

3. The process of claim 1 wherein the reaction temperature is 250°–370° C.

4. The process of claim 1 wherein $d$ is zero.

5. The process of claim 1 wherein $a$, $b$, and $c$ are numbers from 0.01 to 5 and $e$ is from 0 to 1.0.

6. The process of claim 1 wherein $a$ is 1 to 1.5.

7. The process of claim 1 wherein $b$ is 0.1 to 0.5.

8. The process of claim 1 wherein $c$ is 0.1 to 1.0.

9. In a process for the preparation of acrylic acid or methacrylic acid by the oxidation of acrolein or methacrolein, respectively, with molecular oxygen in the vapor phase at a reaction temperature of about 200° C to about 500° C in the presence of an oxide catalyst, and optionally in the presence of steam, the improvement comprising using as the catalyst a catalyst of the formula $$Mo_{12}P_aBi_bCu_cM_dX_eO_f$$

wherein M is at least one element selected from the group consisting of iron, chromium, nickel, manganese, tellurium, palladium, antimony and rhodium;

X is a halogen selected from the group consisting of chlorine, bromine or iodine;

and wherein $a$, $b$ and $c$ are numbers from 0.001–10;

$d$ is from 0–10;

$e$ is from 0.01–0.2; and $f$ is a positive number of oxygens required to satisfy the valence states of the other elements present.

10. In a process for the preparation of acrylic acid or methacrylic acid by the oxidation of acrolein or methacrolein, respectively, with molecular oxygen in the vapor phase at a reaction temperature of about 200° C to about 500° C in the presence of an oxide catalyst, and optionally in the presence of steam, the improvement comprising using as the catalyst a catalyst of the formula $$Mo_{12}P_aBi_bCu_cM_dX_eO_f$$

wherein M is at least one element selected from the group consisting of iron, chromium, nickel, manganese, tellurium, palladium, antimony and rhodium;

X is a halogen selected from the group consisting of chlorine, bromine or iodine; and wherein $a$, $b$ and $c$ are numbers from 0.001–10;

$d$ is from 0–10;

$e$ is 0.01–0.5; and $f$ is a positive number of oxygens required to satisfy the valence states of the other elements present.

11. The process of claim 10 wherein M is at least one element selected from the group consisting of Fe, Cr, and Ni.

12. The process of claim 10 wherein X is chlorine.

13. The process of claim 10 wherein the catalyst employed is $Mo_{12}Bi_{0.5}P_{1.32}Cu_{0.25}Cl_{0.06}O_f$.

14. The process of claim 1 wherein the catalyst is coated on an inert support.

15. The process of claim 14 wherein the catalyst consists essentially of an inert support material having a diameter of at least 20 microns and an outer surface, and a continuous coating of said active catalyst strongly adhering to the outer surface of said support.

16. The process of claim 15 wherein the active catalyst is about 10 to about 100 percent by weight of the inert support.

17. The process of claim 15 wherein the support is selected from the group consisting of silica, alumina, Alundum, alumina-silica, silicon carbide, titania and zirconia.

18. The process of claim 15 wherein the particle size of the inert support is 0.2 cm. to 2 cm.

19. The process of claim 1 wherein methacrolein is reacted.

20. The process of claim 1 wherein acrolein is reacted.

* * * * *